United States Patent [19]

Burch

[11] Patent Number: 5,064,634

[45] Date of Patent: Nov. 12, 1991

[54] METHOD OF FORMING A RADIOACTIVE METALLIC VAPOR

[75] Inventor: William M. Burch, Duffy, Australia

[73] Assignee: I. J. & L. A. Tetley Manuf. Pty. Ltd., Caringbah, Australia

[21] Appl. No.: 519,851

[22] Filed: May 4, 1990

Related U.S. Application Data

[60] Continuation-in-part of Ser. No. 192,221, May 9, 1988, abandoned, which is a division of Ser. No. 784,847, Oct. 4, 1985, abandoned.

[30] Foreign Application Priority Data

Oct. 10, 1984 [AU] Australia .................. PG7486

[51] Int. Cl.$^5$ .................. A61B 6/00; A61K 49/02
[52] U.S. Cl. .................. 424/1.1; 128/659; 423/249
[58] Field of Search .................. 424/1.1; 534/14; 128/659, 671; 423/249

[56] References Cited

U.S. PATENT DOCUMENTS

| | | | |
|---|---|---|---|
| 3,833,469 | 9/1974 | Robson | 424/1.1 X |
| 4,280,991 | 7/1981 | Burch | 424/1.1 |
| 4,938,947 | 7/1990 | Nicolau et al. | 424/1.1 |

OTHER PUBLICATIONS

Evaporation Equipment for Producing radioactive Aerosols, by Wolfgang M. Pusch, *Atomkernenergie* vol. 25, No. 2 (1975) pp. 122, 124.

Primary Examiner—John S. Maples
Attorney, Agent, or Firm—Ladas & Parry

[57] ABSTRACT

A diagnostric device, composition and method of diagnosing airway dysfunction in a patient is disclosed. The apparatus and method require the subjecting of a pharmaceutical acceptable radionuclide, that is the composition, to an elevated temperature in an enclosed space in the presence of either an inert gas or oxygen to produce an inhalable product. The product is inhaled by a patient. A film is located adjacent the airways enabling mapping of the deposition of the radionuclide in the airways of the patient's lungs.

14 Claims, 4 Drawing Sheets

5,064,634

METHOD OF FORMING A RADIOACTIVE METALLIC VAPOR

This is a continuation-in-part of copending application Ser. No. 07/192,221 filed on May 9, 1988, now abandoned, which is a divisional application of U.S. Ser. No. 06/784,847 which was filed on Oct. 4, 1985, now abandoned.

The present application is a continuation-in-part of U.S. application Ser. No. 192,221, filed May 9, 1988 which is a divisional application of U.S. application Ser. No. 784,847 which was filed on Oct. 4,1985.

The present invention relates to new diagnostic compositions, a method for the production of the compositions and apparatus useful in the production of the compositions.

Ventilation and perfusion imaging of the lungs with radionuclides provides the examination of choice for diagnosing airway dysfunction.

Among the radionuclides there exists very few true gases whose properties may be exploited particularly in the diagnosis of airway dysfunction. The use of radiolabelled krypton gas to obtain an airway image has a number of practical disadvantages in use as well as diagnostic limitations. Attempts have been made to stimulate gas-like behaviour in the radionuclide $^{99m}$technetium by creating aerosols from Bernoulli-effect nebulizers or an ultra-fine aerosol by burning a flammable alcohol solution of $^{99m}$technetium.

U.S. Pat. No. 4,380,991 describes a composition comprising a solution containing an alkali metal pertechnetate, such as sodium pertechnetate, in an alcohol such as ethanol. The patent describes the use of the composition as a diagnostic aid for lung disorders. The pertechnetate is introduced as an alcoholic aerosol via a propellant or via combustion to result in a suspension of pertechnetate in carbon dioxide, water vapour and air.

Later developments utilise a system to nebulise a technetium solution to obtain a dispersion of particles, having an average particle size of about 0.06 micron radius. Studies on the particles suggest that the compound produced comprises a technetium oxide ($TcO_7$) which is hydrated with two molecules of water. This is consistent with the particle size distribution and other data.

The advantages of such a composition are that the particles can be easily taken into the lung by normal tidal breathing to achieve a good image so that the resultant image reflects a true small airways deposition pattern.

The present invention represents an improvement over the above two methodologies.

In one form, the present invention provides a diagnostic composition comprising an inhalable composition which includes a pharmaceutically acceptable radionuclide or radioisotope and a pharmaceutically acceptable gaseous diluent.

Preferably, the gaseous diluent is an inert gas, such as argon or neon. Alternatively, or additionally, the diluent may comprise a gas having oxygen as a constituent.

Preferably the radionuclide is a compound of $^{99m}$technetium. The term "radionuclide" refers to the atomic species and therefore includes the element per se or compounds of the radionuclide, such as technetium oxide and technetium carbide. Other suitable volatile radionuclides are $^{125}I$, $^{113m}In$, $^{131}I$ or $^{111}In$.

The present invention also provides a method for producing an inhalable diagnostic composition suitable in the diagnosis of airway dysfunction by depositing a pharmaceutically acceptable radionuclide onto a carbon crucible or element, then subjecting the crucible or element to resistive heating.

The invention further provides apparatus which is useful in the production of the diagnostic composition of the present invention. The apparatus comprises a diagnostic device comprising a generally sealed chamber, a mounting located within said chamber, said mounting being adapted to receive a (preferably carbon) crucible or element for supporting a non-volatile radionuclide, means for heating said radionuclide to cause at least partial vaporisation thereof so that vapour therefrom is diffused within said chamber, a first duct extending from said chamber through which said vapour may be delivered from within said chamber, and valve means to open and close said first duct to selectively control the delivery of said vapour from said chamber.

In a preferred form of the invention, $^{99m}$technetium is heated on a carbon crucible or element under a reducing atmosphere, such as in the presence of an inert gas, to elevated temperatures, in the region of at least 1900° C., more preferably to at least 2200° C. to produce an inhalable composition.

Alternatively, $^{99m}$technetium may be heated in the presence of oxygen.

In the method of the present invention, the vaporised radionuclide is inhaled by a patient and a gamma camera is used to map the deposition of the radionuclide in the patient's airways. This mapping of the airways produces a picture of the usable airway of the patient and thus can be used to detect airway dysfunction particularly obstructive or restrictive pulmonary diseases, such as emphysema and pulmonary fibrosis.

The method of the present invention can be used in conjunction with typical perfusion techniques. For example, radio-labelled human serum albumin is ingested by the patient and the labelled protein collects in the arteries around the lung. This perfusion technique can be used to diagnose pulmonary dysfunction. The combination of the ventilation map and the perfusion map allows an accurate picture of airway dysfunction and can be used in particular to diagnose pulmonary embolus.

The present invention, because of its versatility, allows the selection of a number of suitable radionuclides. These include indium-113 m, $^{99m}$technetium as well as Iodine-131. However, $^{99m}$technetium is the preferred radionuclide species.

Both $^{113m}$indium and $^{99m}$technetium are common radionuclides used for diagnostic purposes and are produced free of carrier, and therefore present no toxicity problems with the levels needed to be inhaled by humans. The radiation doses also would be less than that delivered by a normal chest X-ray and for $^{99m}$technetium would be of the same order as that delivered by existing diagnostic techniques.

A preferred form of the apparatus of the present invention will now be described by way of example with reference to the accompanying drawings wherein.

Figure 1:
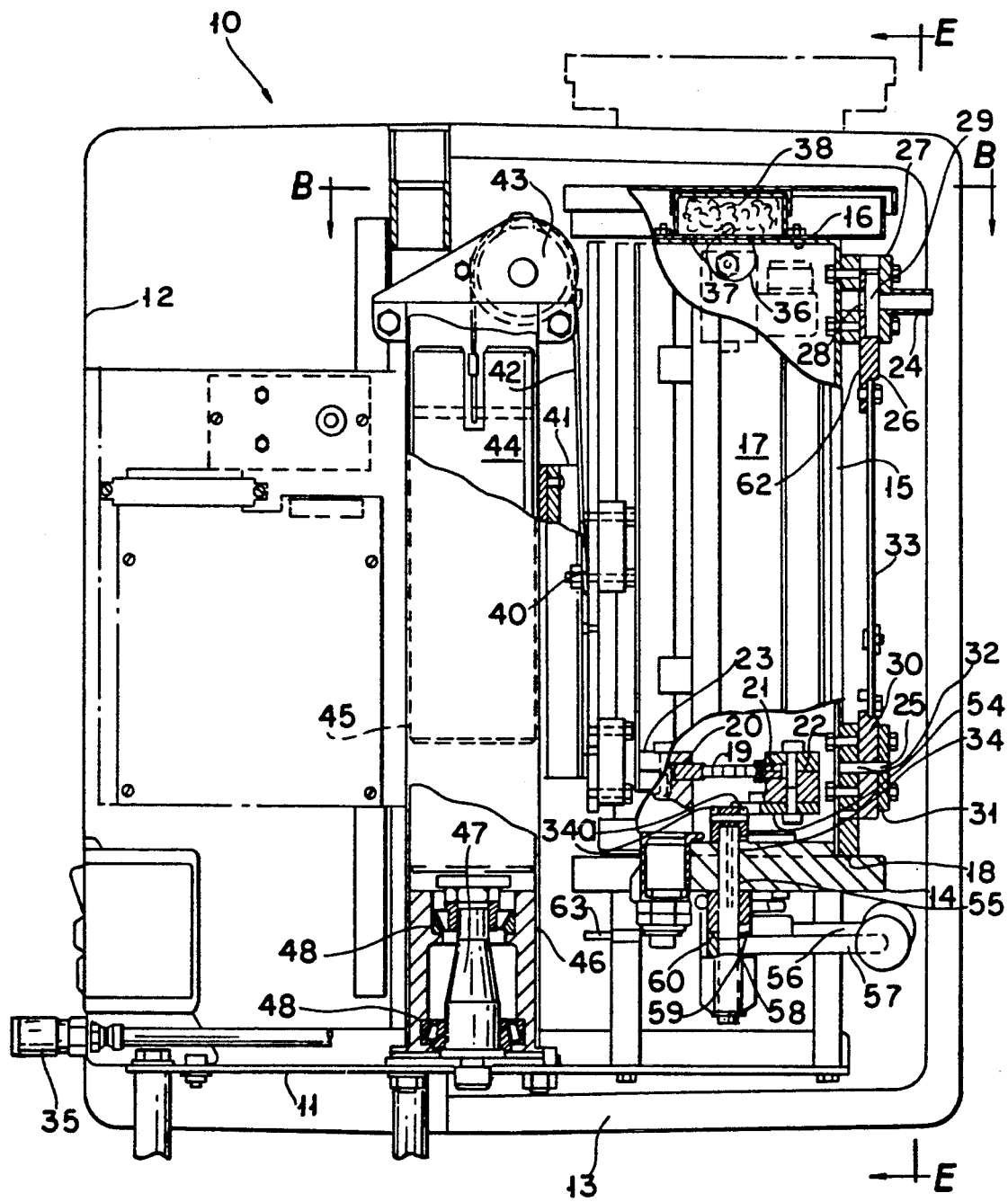
FIG. 1 is a schematic part section side elevation of a diagnostic device.
Figure 2:
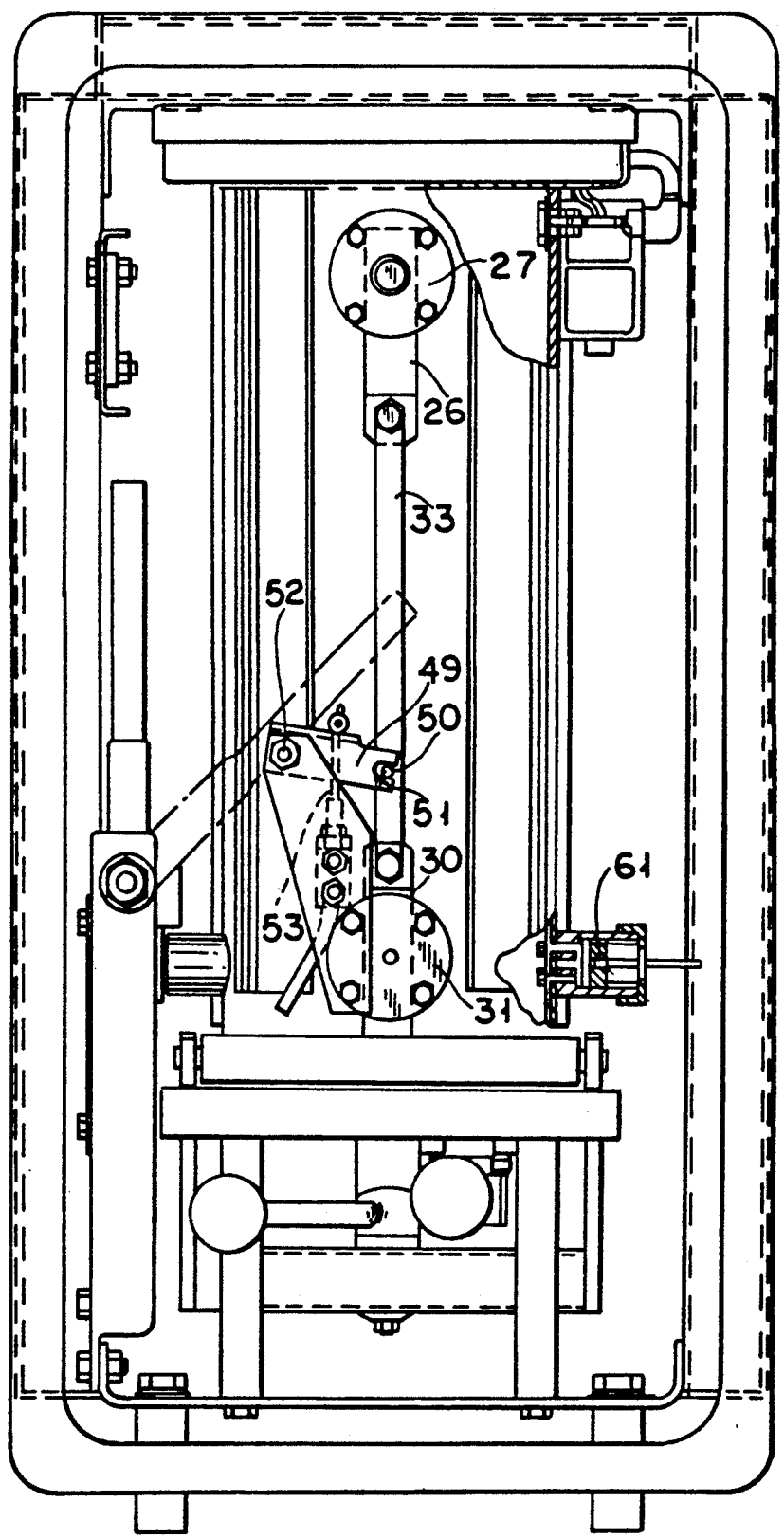
FIG. 2 is a schematic part section end elevation of the device of FIG. 1.
Figure 3:
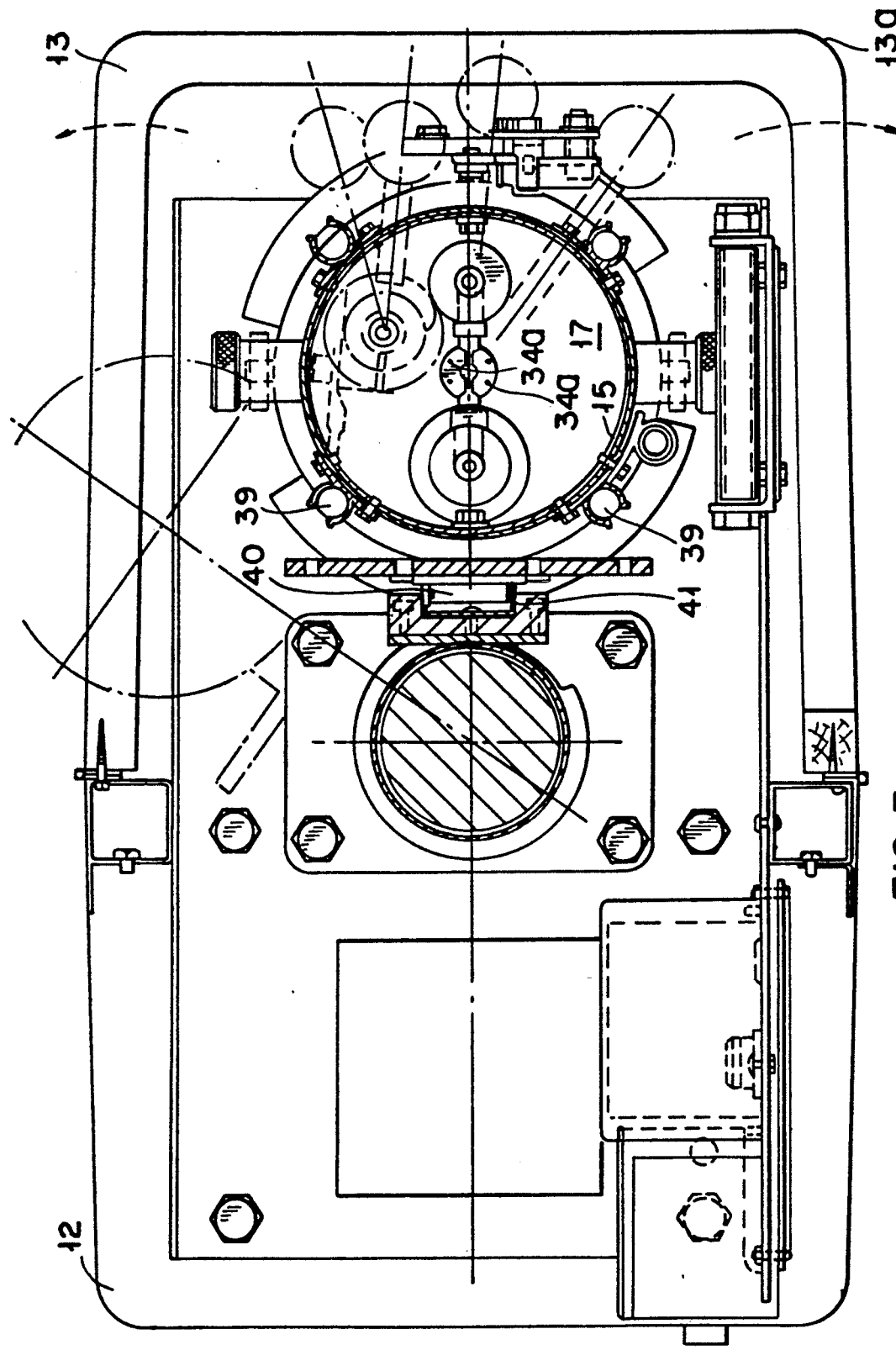
FIG. 3 is a schematic part section top plan view of the device of FIG. 1 sectioned along the line B—B.
Figure 4:
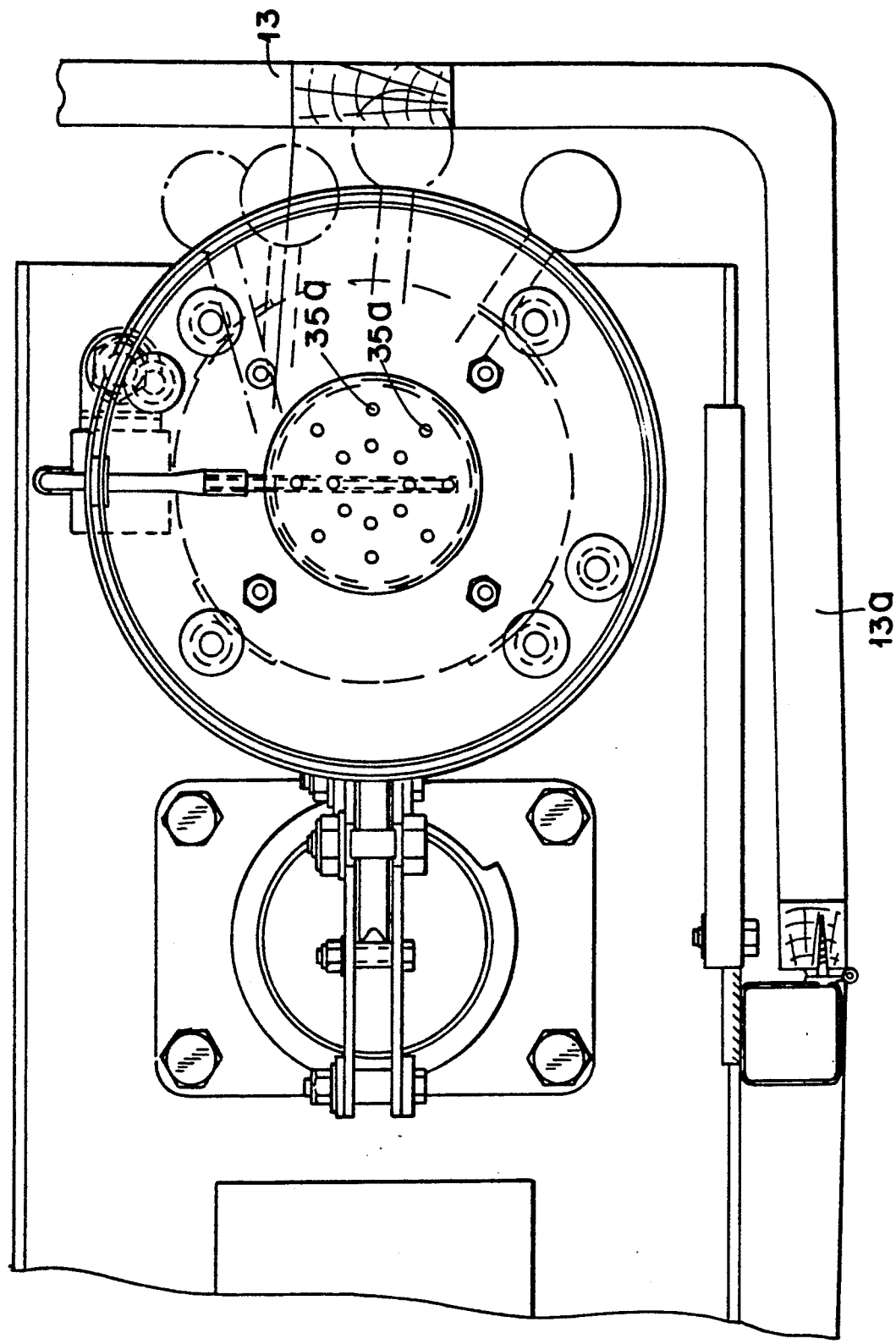
FIG. 4 is a schematic part section top elevation of the device of FIG. 1 sectioned along the line A—A.

In the accompanying drawings a preferred diagnostic device 10 aids in performing a diagnostic method. The device 10 has a base 11 upon which there is mounted a first cover 12. Two further covers 13 and 13A are pivotally mounted on the cover 12 so as to co-operate therewith to selectively enclose the operative portions of the device 10. Mounted on the base 11 is a base plate 14 upon which there is mounted a cylindrical sleeve 15. The sleeve 15 is closed at its upper end by an end cap 16 so that in co-operation with the base plate 14, the sleeve 15 sealingly encompasses a chamber 17. Located on the base plate 14 is a seal 18 which abuts the lower extremity of the sleeve 15. The cylindrical sleeve 15, together with its end cap 16, may be selectively removed from the base place 14. If so required, catches may be provided so as to clamp the sleeve 15 to the base plate 14.

Located within the chamber 17 is a carbon crucible or element 19 extending between two electrodes 20 and 21. The electrodes 20 and 21 are received within electrode mountings 22 and 23, with the electrode mountings 22 and 23 being electrically isolated and being adapted to pass a current through the carbon crucible 19 to heat the radionuclide mounted thereon. Extending from the chamber 17 is a first duct 24 located adjacent the upper end of the chamber 17. Electric wiring including connections 63 extends from each mounting 22 and 23 to an electric power source. A second duct 25 also communicates with the chamber 17 adjacent the lower end thereof to allow air to replace the air taken from the chamber 17. The duct 24 is selectively closed relative to the chamber 17 by means of a valve member 26 which is slidably mounted in the member 27 which provides the duct 24.

The valve member 26 has an opening 28 which provides for continuity of the duct 24, so that when aligned therewith, vapour located within the chamber 17 may be delivered through the duct 24. The normal operating position of the valve member 26 is depicted in FIG. 1, however it should be appreciated that the valve member 26 can be slidably moved to a position whereat the member 26 can be slidably moved to a position whereat the duct 24 is closed relative to the chamber 17. The valve member 26 is also provided with a cavity 29 which bleeds air into the duct 24, when the duct 24 is closed relative to the chamber 17 to enable the patient to continue to breath without removing the mouth piece or mask connected to the duct 2.

The duct 25 is selectively closed by means of a valve member 30 slidably received in the member 31 which provides the duct 25. The valve member 30 is provided with an opening 32 which selectively provides for the continuity of the duct 25.

The valve members 26 and 30 are coupled by a link 33 so that the valve members 26 and 30 are actuated in unison.

Also communicating with the interior of the chamber 17 is a third duct 34 which is connected to a gas fitting 35 by means of a conduit not depicted. The duct 34 enables the selective delivery to the chamber 17 of an inert gas such as argon. The conduit 34 terminates within the chamber 17 with a plurality of nozzles 34A. The end cap 16 is provided with a plurality of apertures 36 which communicate with a bleed passage 37 via a filter 38.

In order to utilize the device 10, a carbon crucible or element must be prepared. The preferred method is to deposit a liquid solution of sodium pertechnetate onto a carbon crucible and let the liquid evaporate. This leaves a solid sodium pertechnetate residue on the crucible. In the alternative solid sodium pertechnetate may be deposited directly onto the crucible.

Using the apparatus of the present invention, an inhalable composition of $^{99m}$technetium which is ideally suited for the diagnosis of airway dysfunction is produced by resistive heating of a carbon crucible at about 2200° C. The process is known to work at about 1900° C. and at temperatures in excess of 2200° C. At this temperature an inhalable substance is produced in a closed container. However, it is known that technetium does not melt until 2172 degrees, nor carbon until about 3550 degrees. Therefore, it is unlikely that the vapor pressure of the technetium is sufficient to create the effect observed or inhalable composition produced, which composition contains up to 90% of the nuclide. Thus, it is suspected that the actual mechanism may require the formation of "white" carbon which forms as small transparent crystals on the edges of the basal planes of graphite above about 2800° C. This allotrope might be derived from the alpha form of graphite which is created from the more abundant beta type on heating above 1000 degrees.

In operation of the abovedescribed device 10, the sleeve 15 is exposed by pivoting the two cover portions 13 and 14 apart. Thereafter the sleeve 15 is removed from the base plate 14 and the carbon crucible 19 placed between the electrodes 20 and 21. The sleeve 15 is then placed back on the base plate 14 so as to provide the generally sealingly closed chamber 17. The valve members 26 and 30 are placed so as to close their respective ducts 24 and 32. The inert gas is then delivered to the chamber 17 and the air bled therefrom via the bleed passage 37. A mouthpiece is connected to the member 27 in order to enable the patient to breath through the passage 24 to inhale air via the cavity 29. This enables the patient to become used to the device 10 prior to actual use. Once the chamber 17 is filled with the inert gas, and the patient is generally ready, a current is delivered to the electrodes 20 and 21.

The vapour then is diffused within the chamber 17. When the patient is ready, the valve members 26 and 30 are moved so that the patient's lungs are now connected to the chamber 17. As the patient continues breathing, the vapours enter the patient's lungs as described previously. This process continues until all the vapour and inert gas are removed from the chamber 17. As the inert gas and vapour is removed from the chamber 17, air is allowed to be bled into the chamber 17 via the passage 25.

Where only an inert gas such as argon is used in chamber when the vapour is formed, the resulting inhalable composition tends to reside in the lungs indefinitely. As the half-life of the technetium is about 6 hours, an image may be obtained for hours after inhalation. It has been found that where even a very small amount of oxygen is introduced into the sealed chamber prior to vaporisation, the resulting inhalable composition behaves differently.

When oxygen is present, the time during which the inhalable composition resides in the lungs is greatly diminished. Even with very diluted oxygen in the chamber, the clearance time of the composition in the lungs appears to correspond to a half-life of about 6 minutes. This short clearance time is ideally suited for diagnosing the pathological processes of the alveolar capillary membrane, as extended clearance times generally indicate an abnormality. The preferred oxygen content of the gas in the chamber (using this second technique) is about 3%. Lesser concentrations can be used. Greater concentrations can be used but may result in the formation of excess carbon oxides such as carbon monoxide and dioxide, which are considered unwanted constituents of the inhalable composition.

In order to inhibit depositing of the radionuclide on the internal surface of the sleeve 15, heating elements 39 may be provided. An electric current is delivered to the heating elements 39 in order to preheat the chamber 17. To facilitate removal of the sleeve 15 from the base plate 14, the sleeve 15 is mounted on a support 40 which is vertically slidably received within a tract 41. Extending from the support 40 is a cable 42 which passes over a sheath 43. On extremity of the cable 42 is attached to a counterweight 44 so that the sleeve 15 is easily held in a raised position relative to the base plate 14. The counterweight 14 is received within a tubular member 45 supported on a bearing member 46. The bearing member 46 is in turn supported on a spigot shaft 47 by means of bearings 48. Accordingly, in operation, the sleeve 15 is moved upward away from the base plate 14 in order to expose the crucible 19. Thereafter the sleeve 15 can be pivoted by use of the bearings 48 to a position whereat the crucible 19 is fully exposed and may be easily removed and replaced. Movement of the sleeve 15 can only take place when the cover parts 13 and 14 are pivoted so as to fully expose the sleeve 15.

Connected to the link 33 in order to facilitate movement thereof is an actuating arm 49 slidably engaging a pin 50 fixed to the link 33. The pin 50 is slidably received within a slot 51 of the arm 49. The arm 49 is pivoted by means of a bolt 52. To cause pivoting movement of the arm 49 a cable 53 is provided which extends to an operator manipulable lever external of the cover 12.

To facilitate easy replacement of the crucible 19, the mounting 22 is supported on a rotatable arm 54 fixed to a shaft 55. The arm 54 is caused to pivot via rotation of the shaft 55 upon actuation of the lever 56. To clamp the shaft 55 in a required position, a further lever 57 is attached to a clamp member 58 which has a cam surface 59. The cam surface 59 co-operates with a further cam surface 60 fixed to the shaft 55. Upon rotation of the cam surface 59 via operation of the lever 57, the shaft 55 may be clamped to the base plate 14.

To ensure that the radionuclide reaches the temperature necessary for vaporisation, a sensor 61 is directed at the crucible 19. The sensor 61 is a photosensitive transistor which is connected to a control circuit which controls the delivery of current to the electrode 20 and 21.

The combination of the ventilation technique in accordance with the present invention together with a perfusion technique provides the diagnostician with an accurate picture of the airways and aids the diagnostician in ascertaining airway dysfunction. In the absence of an accurate ventilation pattern, perfusion diagnoses can be misleading. Therefore, not only does the technique of the present invention aid in the detection of ventilation defects such as obstruction, growth or loss of function in certain areas of the lungs, but it also aids in more accurately diagnosing pulmonary dysfunction.

In typical clinical trials, about 5.0 mCi of $^{99m}$technetium in the form of sodium pertechnetate is deposited onto the carbon crucible of the apparatus of the present invention and the crucible is heated in a sealed chamber to a temperature of about 2200° C. The resulting composition is inhaled by the patient from the apparatus and subsequently a gamma camera photograph is taken of the lungs both from the front and back. The resulting photograph provides a ventilation pattern of the patient's airways as described above.

This method may be performed using either an inert gas, or gas having oxygen as a constituent, as the gas present in the sealed chamber prior to heating of the crucible. It should be understood that, in accordance with the above disclosure, two distinct compositions are formed, each having a separate behaviour in the lungs.

While the above method has been described with reference to a particular apparatus and particular preferred materials and procedures, these should be understood to have been provided as useful examples and not as limitations to the scope of the claims.

The claims defining the invention are as follows:

1. A method of forming an inhalable radioactive composition comprising the steps of:
   depositing a solid form of technetium onto a carbon crucible; and
   heating the carbon crucible to at least 1900° C. in a sealed container.

2. The method of claim 1, wherein the solid form of technetium is sodium pertechnetate.

3. The method of either of claims 1 or 2, wherein the crucible is heated to at least 2200° C.

4. The method of claim 1, wherein the crucible is heated in the presence of a substantially pure inert gas within the sealed container.

5. The method of claim 4 where the inert gas is argon.

6. The method of claim 1, wherein the crucible is heated in the presence of oxygen within the sealed container.

7. The method of claim 6, wherein the oxygen concentration with the sealed chamber is 3% or less.

8. A method of forming an inhalable radioactive composition comprising the steps of:
   depositing a liquid solution of technetium onto a carbon crucible;
   evaporating the liquid so a solid residue remains; and
   heating the carbon crucible to at least 1900° C. in a sealed container.

9. The method of claim 8, wherein the liquid solution of technetium is a liquid solution of sodium pertechnetate.

10. The method of either of claims 8 or 9, wherein the crucible is heated to at least 2200° C.

11. The method of claim 8, wherein the crucible is heated in the presence of a substantially pure inert gas within the sealed container.

12. The method of claim 11 where the inert gas is argon.

13. The method of claim 8, wherein the crucible is heated in the presence of oxygen within the sealed container.

14. The method of claim 13, wherein the oxygen concentration with the sealed chamber is 3% or less.

* * * * *